United States Patent
Ou Yang et al.

(10) Patent No.: US 6,949,228 B2
(45) Date of Patent: Sep. 27, 2005

(54) STERILIZING PHOTO CATALYST DEVICE OF AIR CONDITIONER

(76) Inventors: Chieh Ou Yang, No. 22, Alley 47, Lane 115, Sec. 2, Cheng Kung Rd., Taipei (TW); Wei Ou Yang, No. 24, Alley 47, Lane 115, Sec. 2, Cheng Kung Rd., Taipei (TW)

(*) Notice: Subject to any disclaimer, the term of this patent is extended or adjusted under 35 U.S.C. 154(b) by 443 days.

(21) Appl. No.: 10/200,170

(22) Filed: Jul. 23, 2002

(65) Prior Publication Data

US 2004/0018125 A1 Jan. 29, 2004

(51) Int. Cl.$^7$ ................................................ B01J 19/08
(52) U.S. Cl. .................................... 422/186.3; 422/121
(58) Field of Search .............................. 422/186.3, 121

(56) References Cited

U.S. PATENT DOCUMENTS 5,919,422 A * 7/1999 Yamanaka et al. .......... 422/121
6,663,814 B2 * 12/2003 Kondou et al. ............. 264/239

* cited by examiner

Primary Examiner—Kishor Mayekar
(74) Attorney, Agent, or Firm—Rosenberg, Klein & Lee

(57) ABSTRACT

A sterilizing photo catalyst device of air conditioner, wherein one or more ultraviolet (UV) light-emitting diodes (LEDs) are installed at the passageway mouth, the intake, or the outlet of an air conditioner. The UV LEDs can thus be placed at one side of a filter net and a photo catalyst attached together to save a holder for supporting the photo catalyst net, hence simplifying the whole structure. Simultaneously, the UV LEDs are connected in parallel. When one of the UV LEDs malfunctions, the rest of UV LEDs still can work and partly function properly. Moreover, because no ICs are required in the whole circuit, the cost is lower.

9 Claims, 17 Drawing Sheets

STERILIZING PHOTO CATALYST DEVICE OF AIR CONDITIONER

FIELD OF THE INVENTION

The present invention relates to a sterilizing photo catalyst device of air conditioner and, more particularly, to a sterilizing photo catalyst device of air conditioner, which has a simple structure and high sterilization efficiency, and can be continuously and repetitively used.

BACKGROUND OF THE INVENTION

Recently, along with enhancement of life standard for people, air conditioners have become common electrical appliances.

When an air conditioner is in use for some time, a large amount of dusts will accumulate at the filter net or the heat-radiating fins, and condensed water will also infest in the air conditioner. The malodor will be generated, especially when air conditioner is not used for a period of time. Some people may soon feel dizzy or even nauseate and vomit after staying in an air-conditioned room.

Therefore, bacteria and mildew will circulate indoors along with hot and cold air to reduce the working efficiency of the air conditioner, increase the power consumption, and even contaminate indoor air. Therefore, how to clean and sterilize air conditioners effectively and timely becomes an urgent problem to be solved.

In addition to the filter net, an ultraviolet (UV) lamp tube is added in the present air conditioner. The UV lamp tube has sterilizing function, and can also restore the function of a photo catalyst net. However, because the UV lamp tube is a cathode glass lamp tube easily breakable to harm people, it is usually sheathed by a tetrachloroethylene tube for protection, hence having a higher cost. Moreover, because it contains mercury, the problem of environmental pollution may arise. As shown in FIG. 1, a conventional sterilizing device of air conditioner is formed by series connecting a voltage regulation IC 1a with several light-emitting diodes 2a. The light-emitting diodes 2a are placed between a filter net 3a and a photo catalyst net 4a. Because the light-emitting diodes 2a are placed between the filter net 3a and the photo catalyst net 4a, a holder (not shown) is required for the photo catalyst net 4a, hence complicating the structure. Moreover, when one of the light-emitting diode 2a malfunctions, the whole function is affected.

Besides, along with aggravation of air pollution, air filter nets have been widely used in air conditioners, air cleaners, and exhaust apparatuses. Conventional photo reduction catalyst fiber is a hybrid unit formed by embedding photo catalyst with titanium dioxide as the primary component into porous substrate like active carbon powder and then mixed on carrier like fiber. For this kind of air filter net having active carbon powder attached thereon, because the hybrid unit has active carbon powder, the content of photo catalyst is low. When in use, the active carbon quickly saturates to attenuate the effect of filtering air. The fiber used as carrier of the hybrid unit of photo catalyst and active carbon powder also easily moistens to expand and deform when used in air conditioners, air cleaners, and refrigerators. Moreover, it cannot be folded and has no function of filter net. Some other conventional air filter nets are made by mold ejection of plastic, wherein photo catalyst is mixed in plastic and then directly contained in the filter net during the procedure of mold ejection. This kind of air filter net is a plastic component, and cannot be folded. Because its gap is too large, it has no function of filter net. Moreover, because the contact area of photo catalyst with air is small, the effect is not good.

SUMMARY OF THE INVENTION

The primary object of the present invention is to provide a sterilizing photo catalyst device of air conditioner, which has a simple structure and a high sterilization efficiency, and can be continuously and repetitively used.

To achieve the above object, the present invention provides a sterilizing photo catalyst device for air conditioner, wherein one or more UV light-emitting diodes (LEDs) are installed at the passageway mouth, intake, or outlet of an air conditioner. The UV LEDs are placed at one side of a filter net and a photo catalyst net attached together to save a holder for supporting the photo catalyst net and thus simplify the whole structure. The UV LEDs are connected in parallel. When one of the UV LEDs malfunctions, the rest of UV LEDs still can work and partly function properly. Moreover, because no ICs are required in the whole circuit, the cost is lower.

The various objects and advantages of the present invention will be more readily understood from the following detailed description when read in conjunction with the appended drawing, in which:

DETAILED DESCRIPTION OF THE PREFERRED EMBODIMENTS

Figure 1:
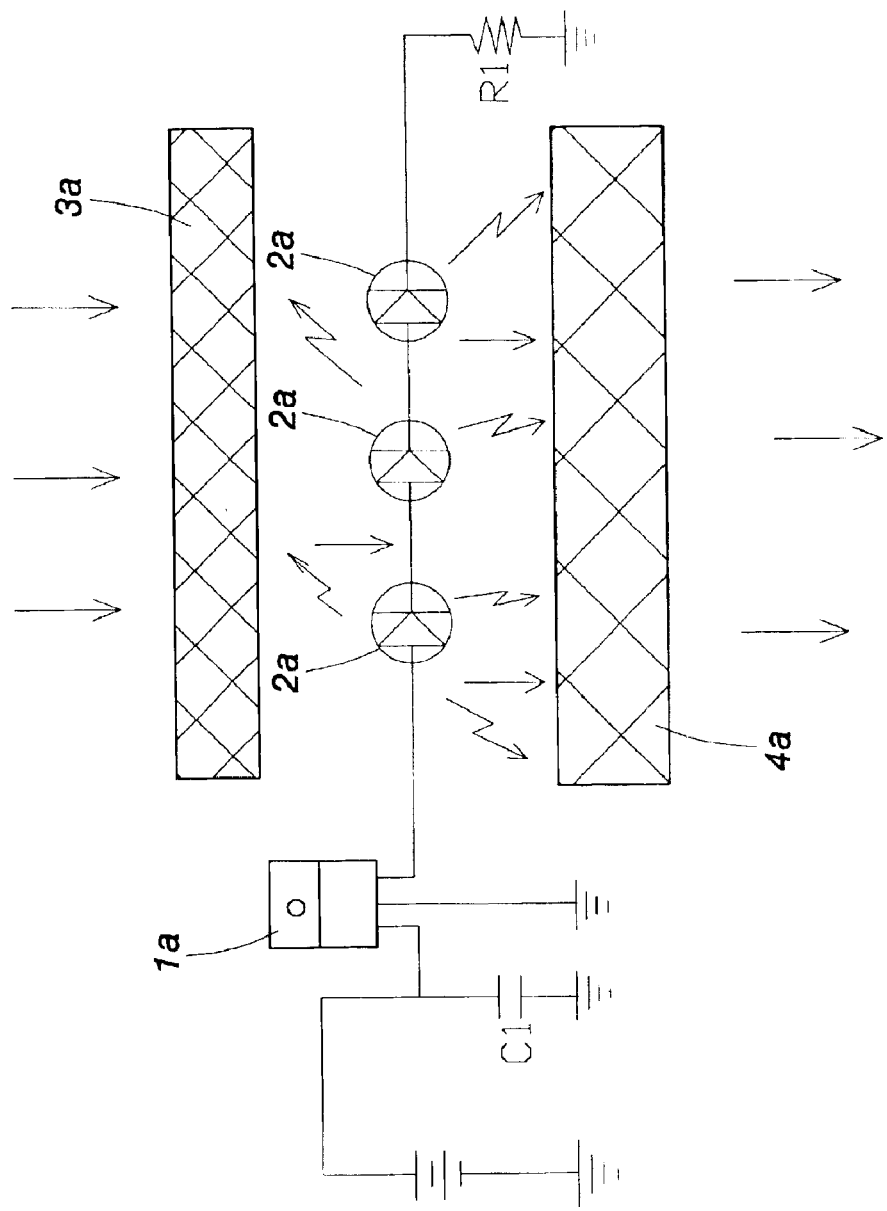
FIG. 1 is a diagram of a conventional sterilizing device of air conditioner.
Figure 2:
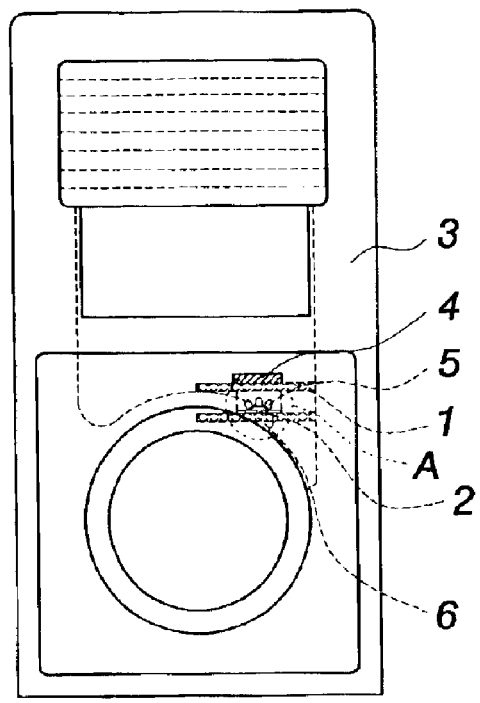
FIG. 2 is a front view of a first embodiment of the present invention.
Figure 2A:
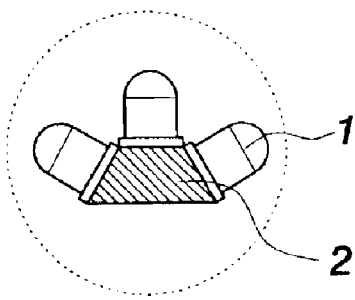
FIG. 2A is a partly enlarged view of part A of FIG. 2.
Figure 3:
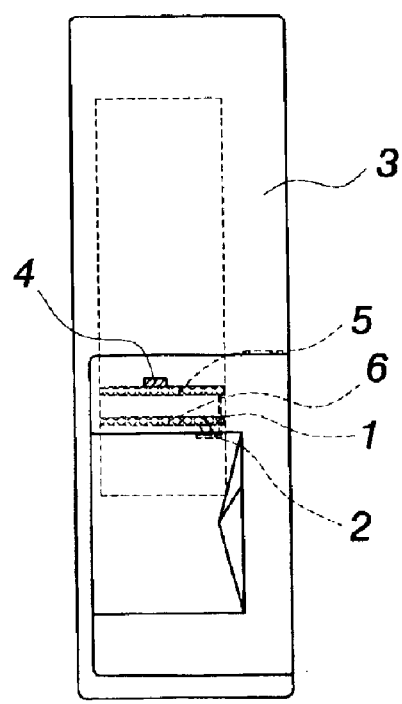
FIG. 3 is a side view of the first embodiment of the present invention.
Figure 4:
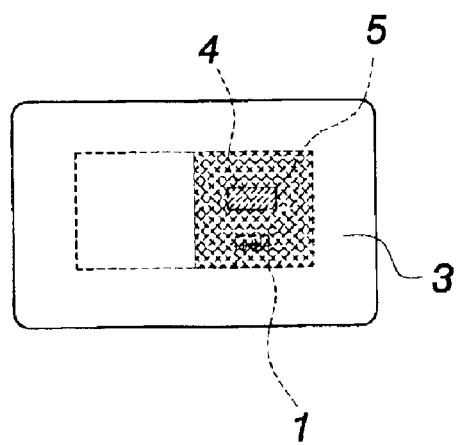
FIG. 4 is a top view of the first embodiment of the present invention.

As shown in FIGS. 2, 3, and 4, the present invention provides a sterilizing photo catalyst device of air conditioner. In this embodiment, three UV LEDs 1 are installed at the passageway mouth of a chest type air conditioner. The UV LEDs 1 (shown in FIG. 2A) pass through a support rack 2 and are fixed on a fixing rack 6 installed in a machine box 3 of the air conditioner, and are located below a filter net 5 and a photo catalyst net 4. The photo catalyst net 4 is attached on the filter net 5. The UV LEDs 1 can irradiate the photo catalyst net 4 in 180 degrees to excite photo catalyst again, and directly sterilize bacteria on the filter net 5. Because the area of the passageway mouth is smaller, the materials of the filter net 5 and the photo catalyst net 4 can be saved. Of course, it is also feasible to only use the filter net 5, the photo catalyst net 4, or a net having both the filtering and photo catalyzing functions.

Figure 5:
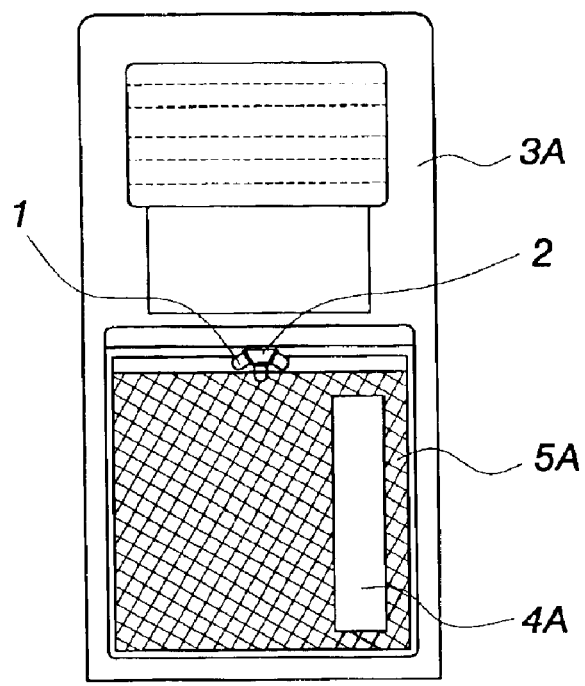
FIG. 5 is a front view of a second embodiment of the present invention.
Figure 6:
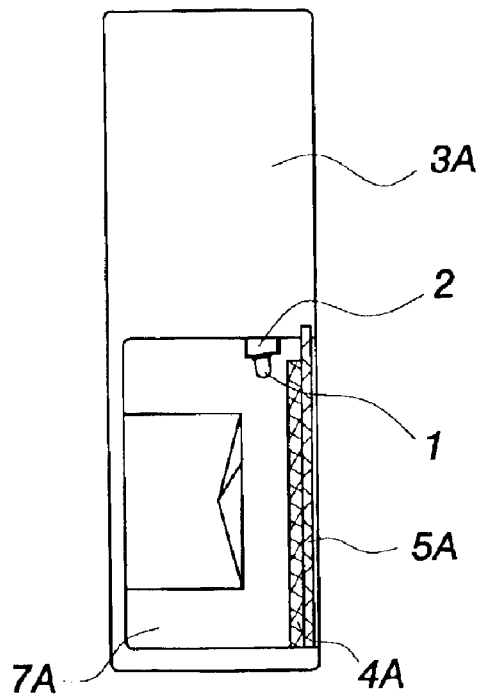
FIG. 6 is a side view of the second embodiment of the present invention.

As shown in FIGS. 5 and 6, in this embodiment, three UV LEDs 1 are installed at the intake of a chest type air conditioner. The UV LEDs 1 pass through a support rack 2 and are fixed in a machine box 3A of the air conditioner. The photo catalyst net 4A is attached on the filter net 5A with adhesive. The UV LEDs 1 are located behind the photo catalyst net 4A and the filter net 5A. The UV LEDs 1 can irradiate the photo catalyst net 4A to excite photo catalyst again, and can also sterilize the air passageway 7A.

Figure 7:
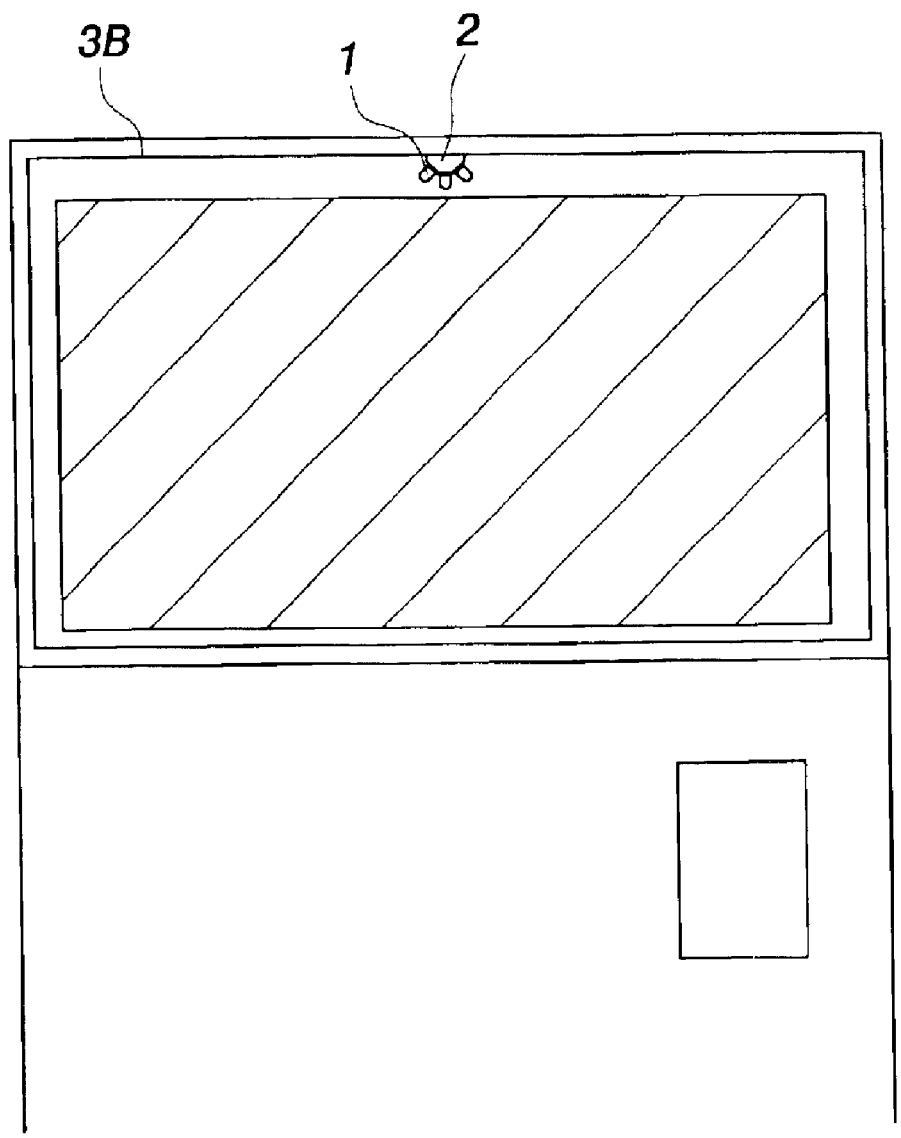
FIG. 7 is a front view of a third embodiment of the present invention.
Figure 8:
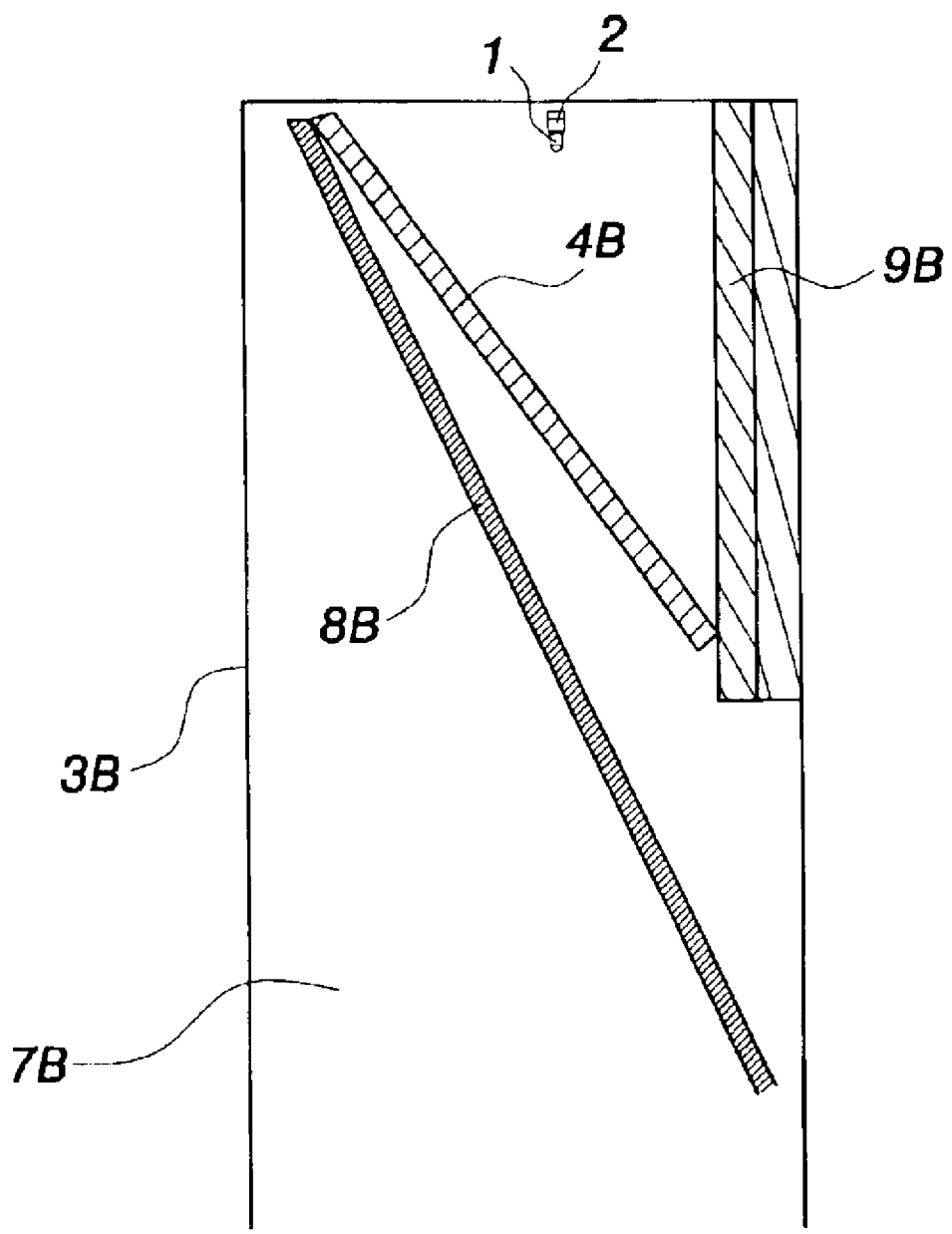
FIG. 8 is a side view of the third embodiment of the present invention.

As shown in FIGS. 7 and 8, in this embodiment, three UV LEDs 1 are installed at the outlet of a chest type air conditioner. The UV LEDs 1 pass through a support rack 2 and are fixed in a machine box 3B of the air conditioner. The photo catalyst net 4B is installed between a condenser face 8B and a wind direction control blade 9B. The UV LEDs 1 are located above the photo catalyst net 4B. The UV LEDs 1 can irradiate the photo catalyst net 4B to excite photo catalyst again, and can also irradiate the condenser face 8B, an air passageway 7B, and the wind direction control blade 9B to accomplish sterilization.

Figure 9:
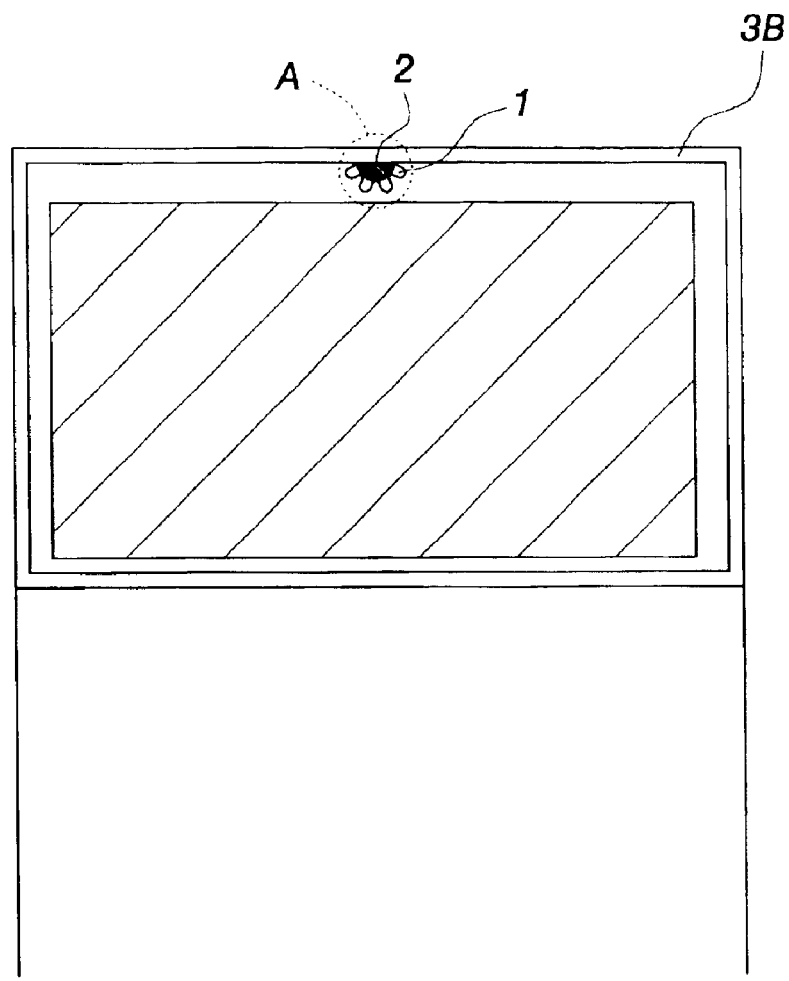
FIG. 9 is a front view of a fourth embodiment of the present invention.
Figure 9A:
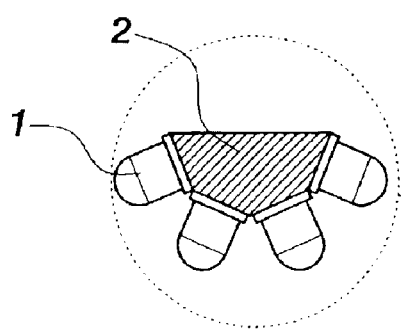
FIG. 9A is a partly enlarged view of part A of FIG. 9.
Figure 10:
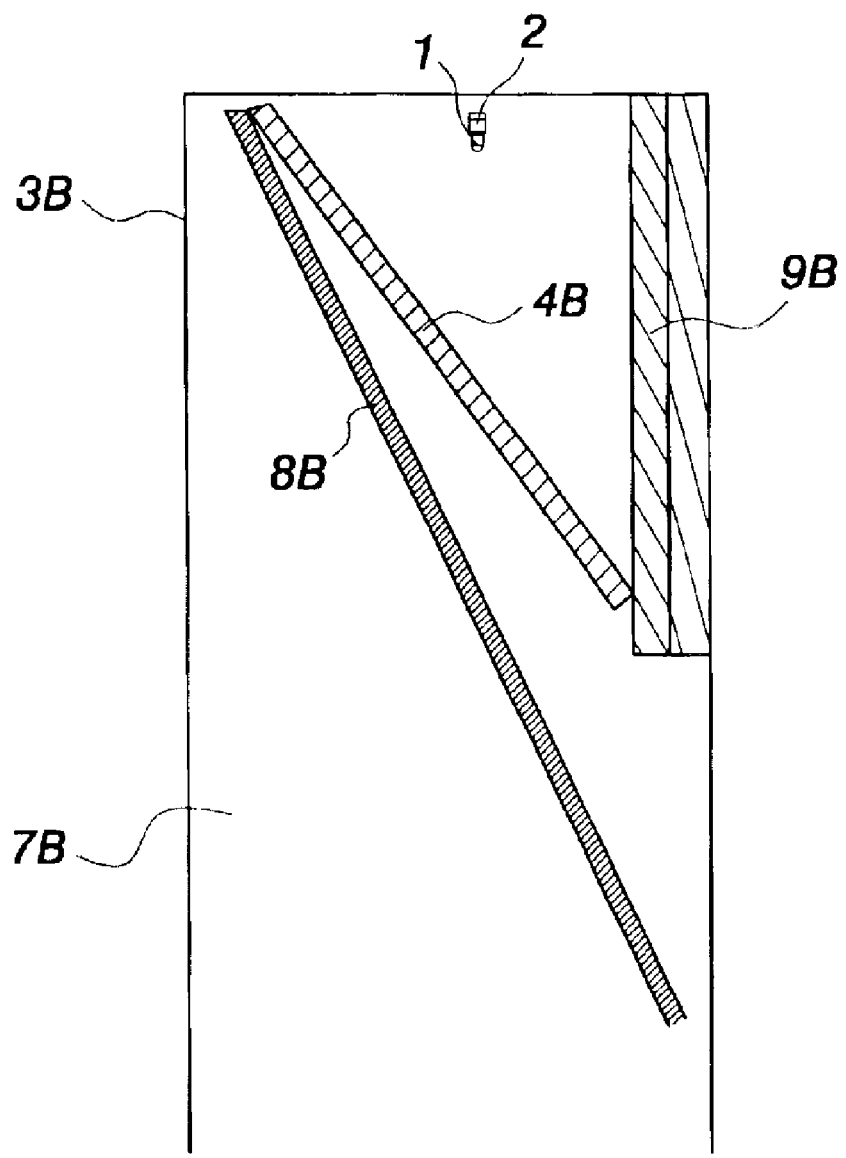
FIG. 10 is side view of the fourth embodiment of the present invention.
Figure 11:
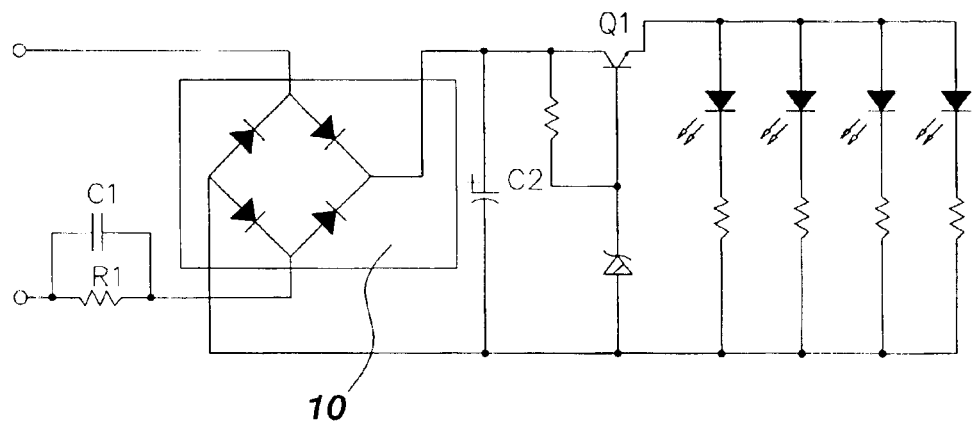
FIG. 11 is a circuit diagram of the fourth embodiment of the present invention.
Figure 12:
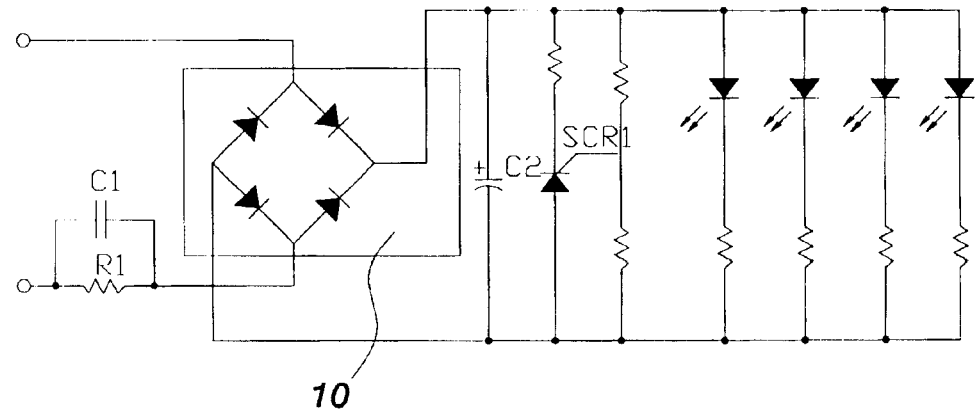
FIG. 12 is another circuit diagram of the fourth embodiment of the present invention.

As shown in FIGS. 9 and 10, in this embodiment, the structure is approximately the same as that of the third embodiment shown in FIGS. 7 and 8. The only difference is that there are four UV LEDs 1 (shown in FIG. 9A) used. Besides, as shown in FIGS. 11 and 12, four UV LEDs 1 are connected in parallel. An AC current flows through a current-limiting step-down capacitor C1, a leakage resistor R1 (or an AC transformer is used), and is then converted into a DC current by a bridge type rectifying circuit 10. The DC current flows through a filtering capacitor C2 and a transistor Q1 or a semiconductor-controlled rectifier SCR1 to the four parallel-connected UV LEDs 1 to form a fixed voltage circuit (or a DC power source provided by a power source indication lamp circuit, a remote-control circuit, or a display circuit). Because it is not necessary to use ICs in this circuit, the cost is lower.

Figure 13:
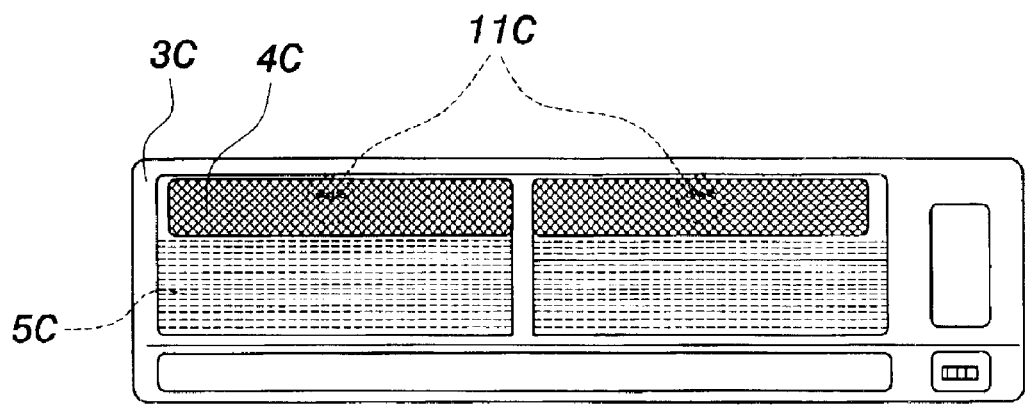
FIG. 13 is a front view of a fifth embodiment of the present invention.
Figure 14:
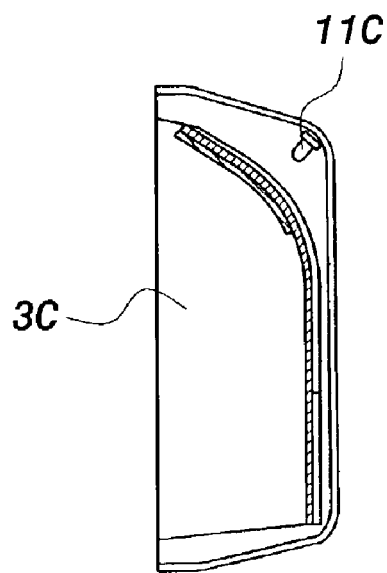
FIG. 14 is a side view of the fifth embodiment of the present invention.

As shown in FIGS. 13 and 14, in this embodiment, two light source sets 11C are installed above the outlet of a separable air conditioner and the top of a machine box of the air conditioner, respectively. Each of the light source sets 11C comprises three UV LEDs 1 passing through a support rack 2. A photo catalyst net 4C is attached on the filter net 5C with adhesive. The two light source sets 11C can irradiate the photo catalyst net 4C to excite photo catalyst again, and can simultaneously irradiate the whole outlet passageway to accomplish sterilization.

Figure 15:
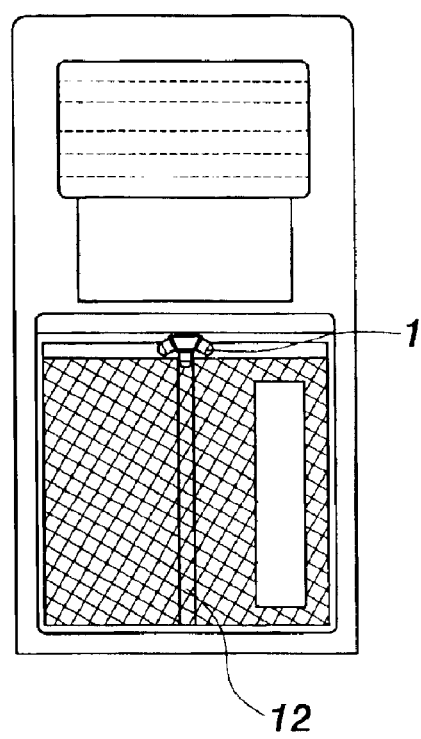
FIG. 15 is a front view of a sixth embodiment of the present invention.
Figure 16:
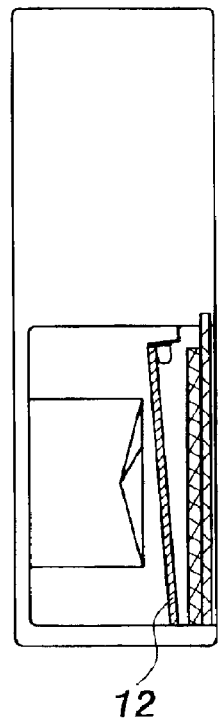
FIG. 16 is a side view of the sixth embodiment of the present invention.

As shown in FIGS. 15 and 16, in this embodiment, the structure is approximately the same as that of the second embodiment shown in FIGS. 5 and 6. The only difference is that a cylindrical reflection bar 12 is disposed on the axis of the UV LEDs 1. Reflected light from the reflection bar 12 is exploited to expand the UV light so as to irradiate the photo catalyst net, the filter net, and the machine box.

Figure 17:
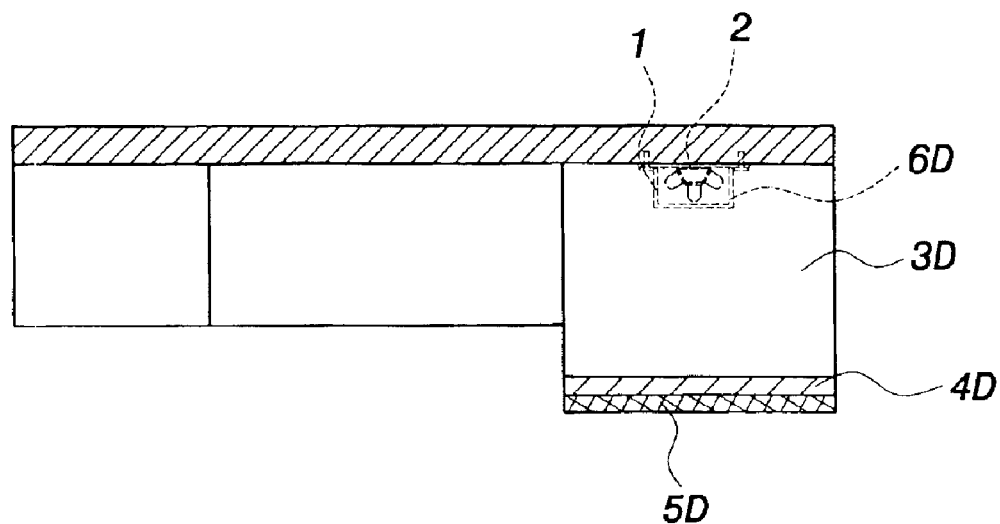
FIG. 17 is a front view of a seventh embodiment of the present invention.
Figure 18:
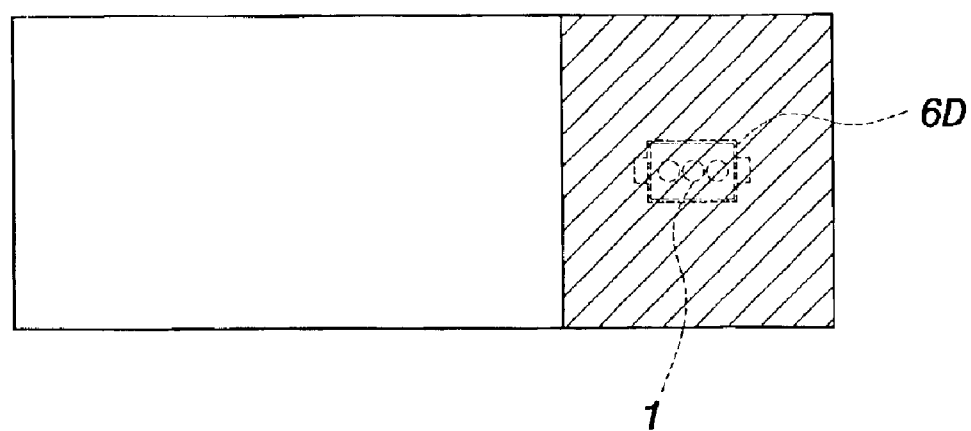
FIG. 18 is a side view of the seventh embodiment of the present invention.

As shown in FIGS. 17 and 18, in this embodiment, three UV LEDs 1 are installed at the intake of a central air conditioner. The UV LEDs 1 pass through a support rack 2 and are fixed on a fixing rack 6D installed in a machine box 3D of the air conditioner, and are located below a filter net 5D and a photo catalyst net 4D. The photo catalyst net 4D is attached on the filter net 5D. The UV LEDs 1 can irradiate the photo catalyst net 4D in 180 degrees to excite photo catalyst again, and directly sterilize bacteria on the filter net 5D. Of course, it is also feasible to only use the filter net 5D, the photo catalyst net 4D, or a net having both the filtering and photo catalyzing functions.

As shown in FIGS. 22 to 25, in these two embodiments, the above UV LEDs 1 are installed at the intake of a car air conditioner. The UV LEDs 1 pass through a support rack 2 and are fixed on a fixing rack 6E or 6F installed in the car air conditioner. A net having both the filtering and photo catalyzing functions is disposed below the UV LEDs 1. The net can be circular or rectangular. The number of the UV LEDs 1 can be increased according to the necessity.

Figure 26:
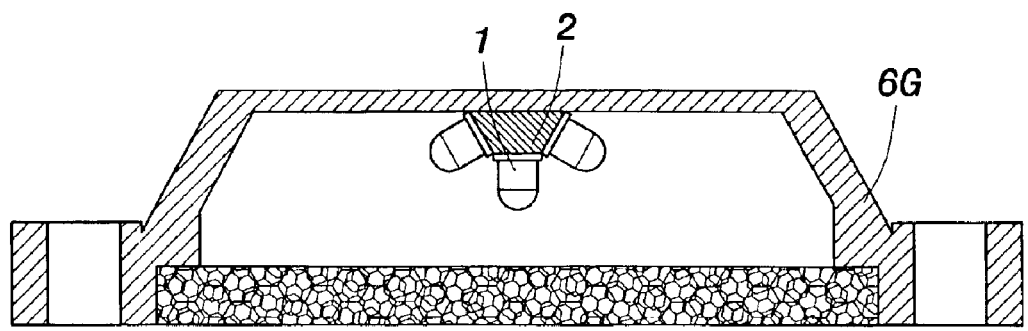
FIG. 26 is a side view of a tenth embodiment of the present invention.
Figure 27:
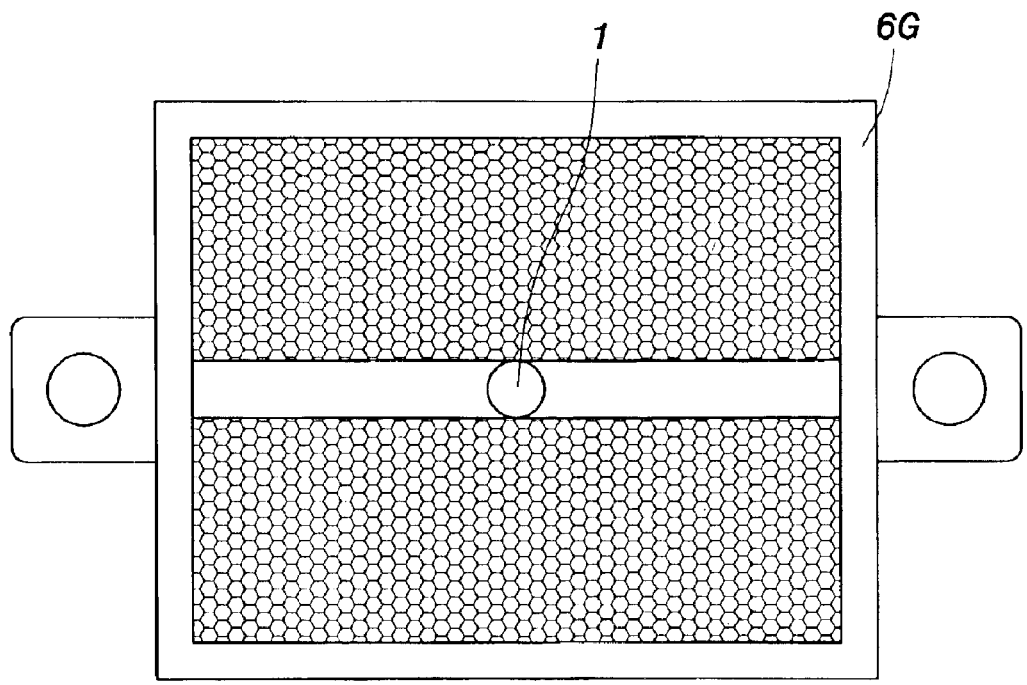
FIG. 27 is a top view of the tenth embodiment of the present invention.

Moreover, as shown in FIGS. 26 and 27, in this embodiment, an air filter net (shown in FIG. 21 and described in detail below) composed of porous substrate is disposed below the UV LEDs 1. The same UV LEDs 1 as the first embodiment (shown in FIG. 2A) pass through a support rack 2 and are fixed on a fixing rack 6G installed in a car air conditioner.

Figure 19:
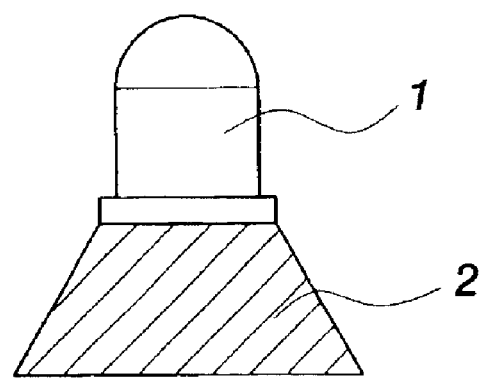
FIG. 19 is a structure diagram of a single UV LED of the present invention.
Figure 20:
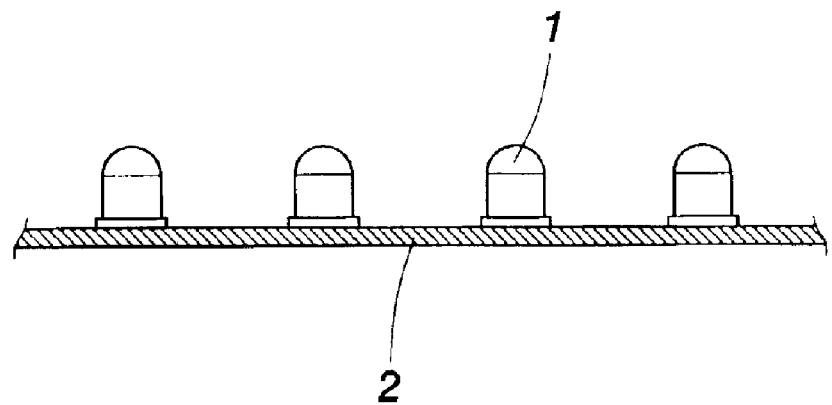
FIG. 20 is a structure diagram of four transversally arranged UV LEDs of the present invention.

In all of the above embodiments, the UV LED 1 can be of single-head type (FIG. 19), three-head type (FIG. 2A), four-head type (FIG. 9A or 20), or a surface-mounted device (SMD). For arrangement of positions, the three-head type UV LEDs 1 are uniformly distributed along an arced plane, and are fixed on the support rack 2 and spaced by an angle of 60 degrees. The four-head type UV LEDs 1 shown in FIG. 9A are uniformly distributed along an arced plane, and are fixed on the support rack 2 and spaced by an angle of 45 degrees. The four-head type UV LEDs 1 shown in FIG. 20 are transversally and equidistantly arranged, and are fixed on a support rack to irradiate the photo catalyst net, the filter net, and the passageway in 180 degrees, thereby achieving a better sterilizing effect.

Furthermore, in order to accomplish sterilizing or filtering effect, the filter net, the photo catalyst net, or the photo catalyst net and the filter net attached together, or a net having both the filtering and photo catalyzing functions can be separately placed at one side of the UV LEDs 1.

Figure 21:
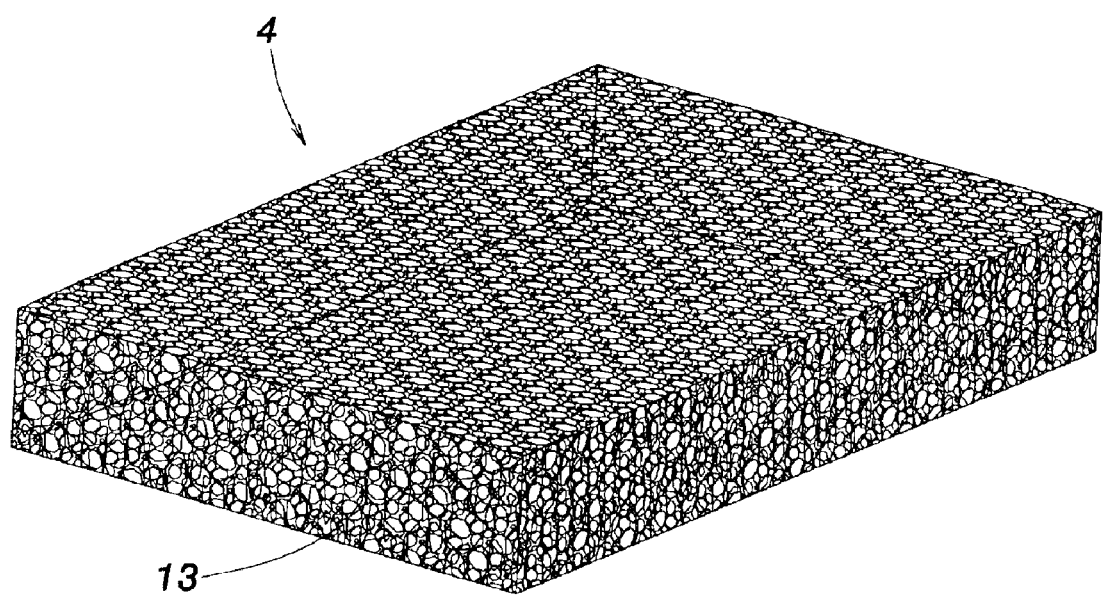
FIG. 21 is a perspective view of a photo catalyst net of the present invention.
Figure 22:
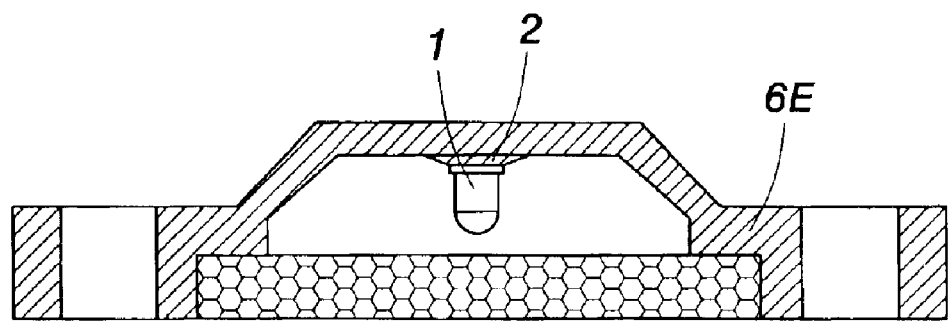
FIG. 22 is a side view of an eighth embodiment of the present invention.
Figure 23:
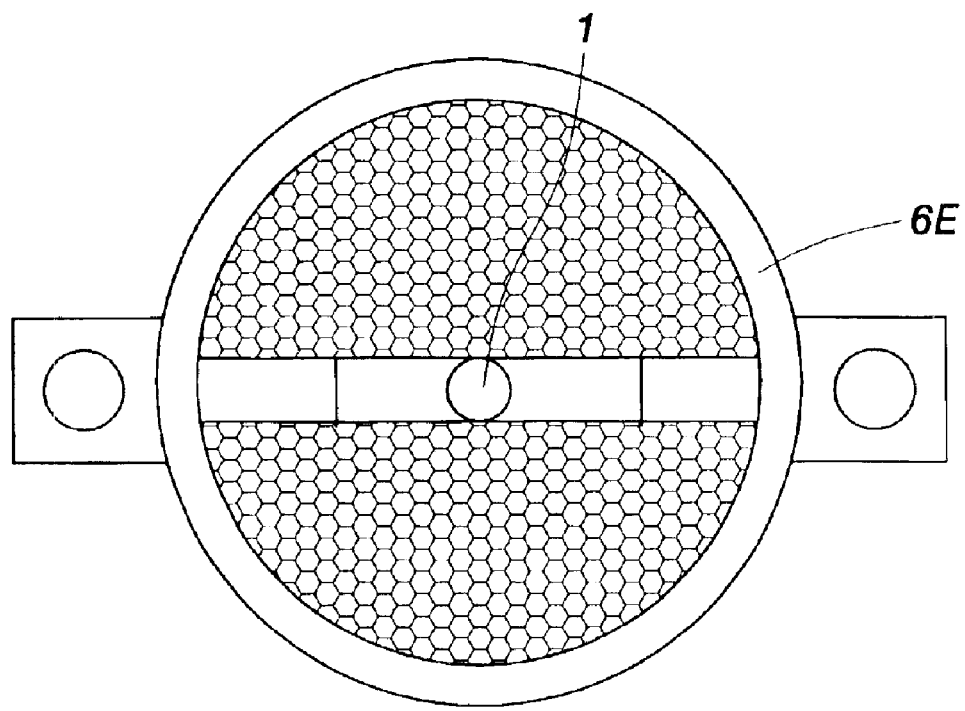
FIG. 23 is a top view of the eighth embodiment of the present invention.
Figure 24:
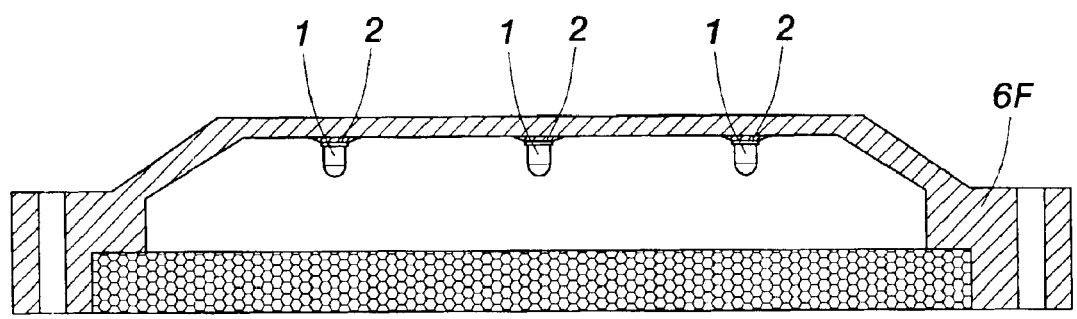
FIG. 24 is a side view of a ninth embodiment of the present invention.
Figure 25:
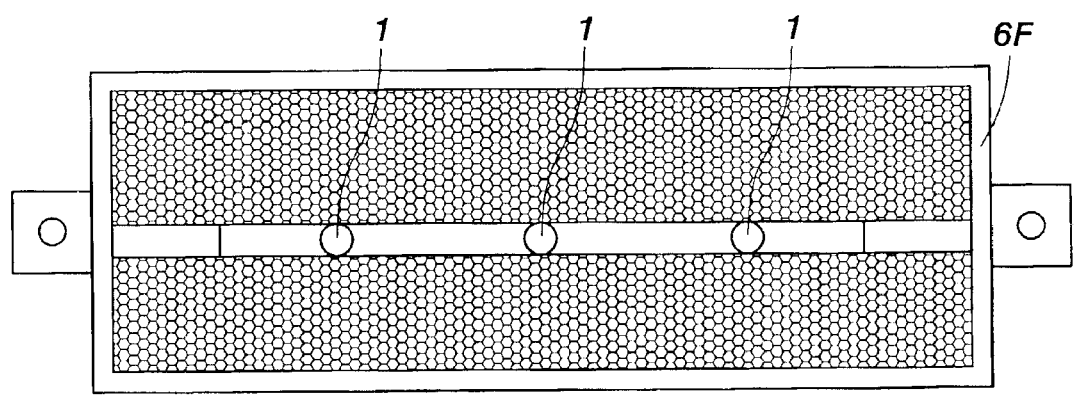
FIG. 25 is a top view of the ninth embodiment of the present invention.

As shown in FIG. 21, in all of the above embodiments, the photo catalyst net 4 is an air filter net composed of porous substrate 13. The substrate 13 is made of soft material like honeycomb sponge. The honeycomb sponge is polyester foam sponge. A layer of photo catalyst (titanium dioxide) is uniformly adhered on the porous fiber surface of the honeycomb sponge. The adhered material does not include the component of active carbon.

There are two ways of adhering photo catalyst onto the photo catalyst net 4.
1. Immersion: The honeycomb sponge is immersed into a photo catalyst solution to uniformly adhere photo catalyst particles onto the porous fiber surface of the honeycomb sponge. The honeycomb sponge is then taken out and dried for use.
2. Glue: The honeycomb sponge is immersed into a photo catalyst solution mixed with air permeable glue to uniformly adhere photo catalyst particles onto the porous fiber surface of the honeycomb sponge. The honeycomb sponge is then taken out and dried for use.

The photo catalyst net 4 formed by using glue to adhere photo catalyst thereon is waterproof. Moreover, because air permeable glue is used, the effect of photo catalyst is not affected.

To sum up, the sterilizing photo catalyst device for air conditioner in the present invention can be placed at one side of a filter net and a photo catalyst attached together to save a holder for supporting the photo catalyst net, hence simplifying the whole structure. Simultaneously, the UV LEDs are connected in parallel. When one of the UV LEDs malfunctions, the rest of UV LEDs still can work and partly function properly. Moreover, because no ICs are required in the whole circuit, the cost is lower. The photo catalyst net 4 uses soft material like honeycomb sponge as the substrate 13 to let photo catalyst be uniformly adhered on the surface of the substrate 13. Therefore, the photo catalyst net is also a filter net, and includes photo catalyst. The photo catalyst net is foldable, has good sterilizing and filtering effect, is waterproof, and has a large contact area with air. Moreover, the photo catalyst net can be repetitively used after gently washing out dusts on the filter net with water.

Although the present invention has been described with reference to the preferred embodiment thereof, it will be understood that the invention is not limited to the details thereof. Various substitutions and modifications have been suggested in the foregoing description, and other will occur to those of ordinary skill in the art. Therefore, all such substitutions and modifications are intended to be embraced within the scope of the invention as defined in the appended claims.

We claim:

1. A sterilizing photo catalyst device for an air conditioner, comprising:
   a plurality of ultraviolet light-emitting diodes electrically connected in parallel with one another and installed at a passageway mouth, an intake, or an outlet of the air conditioner; and
   a photo catalyst net in contact with a filter net of the air conditioner;
   wherein the ultraviolet light-emitting diodes irradiate the photo catalyst net with ultraviolet light to sterilize thereby a plurality of micro-organisms on said filter net, whereby air leaving the air conditioner is substantially clean.

2. The sterilizing photo catalyst device for an air conditioner as claimed in claim 1, wherein said ultraviolet light-emitting diodes are placed at one side of a net having both a filtering function and a photo catalyzing function.

3. The sterilizing photo catalyst device for an air conditioner as claimed in claim 1, wherein said ultraviolet light-emitting diodes are positioned on a side of a photo catalyst net of said air conditioner.

4. The sterilizing photo catalyst device for an air conditioner as claimed in claim 3, wherein said photo catalyst net of said air conditioner comprises a porous substrate with a photo catalyst uniformly adherent to a surface thereof, said substrate being made of a soft material.

5. The sterilizing photo catalyst device for an air conditioner as claimed in claim 4, wherein said substrate is a honeycomb sponge.

6. The sterilizing photo catalyst device for an air conditioner as claimed in claim 5, wherein said honeycomb sponge is a polyester foam sponge.

7. The sterilizing photo catalyst device for an air conditioner as claimed in claim 4, wherein said ultraviolet light-emitting diodes are positioned as an array chosen from the group consisting of three-headed arrays and four-headed arrays.

8. The sterilizing photo catalyst device for an air conditioner as claimed in claim 1, wherein said ultraviolet light-emitting diodes are transversely and equidistantly arranged.

9. The sterilizing photo catalyst device for an air conditioner as claimed in claim 1, wherein said ultraviolet light-emitting diodes are uniformly arranged along an arcuate plane.

* * * * *